United States Patent
Pfeiffer et al.

(10) Patent No.: US 8,235,722 B2
(45) Date of Patent: Aug. 7, 2012

(54) METHOD OF PRODUCING A DENTAL PROSTHETIC ITEM, AND DENTAL PROSTHETIC ITEM THUS PRODUCED

(75) Inventors: Joachim Pfeiffer, Bensheim (DE); Wilhelm Schneider, Grasellenbach (DE); Norbert Thiel, Bad Saeckingen (DE)

(73) Assignees: Sirona Dental Systems GmbH, Bensheim (DE); Vita Zahnfabrik H. Rauter GmbH Co. KG, Bad Säckingen (DE)

( * ) Notice: Subject to any disclaimer, the term of this patent is extended or adjusted under 35 U.S.C. 154(b) by 749 days.

(21) Appl. No.: 11/205,019

(22) Filed: Aug. 17, 2005

(65) Prior Publication Data
US 2006/0257823 A1    Nov. 16, 2006

(30) Foreign Application Priority Data
May 13, 2005  (DE) .......................... 10 2005 023 105

(51) Int. Cl.
*A61C 5/08*    (2006.01)
(52) U.S. Cl. ........................................ 433/183; 433/218
(58) Field of Classification Search .................. 433/172, 433/173, 180, 183, 218, 223, 226
See application file for complete search history.

(56) References Cited

U.S. PATENT DOCUMENTS

| | | | |
|---|---|---|---|
| 4,585,417 A * | 4/1986 | Sozio et al. ................ | 433/202.1 |
| 4,650,418 A | 3/1987 | Blair et al. | |
| 4,877,402 A * | 10/1989 | Hirabayashi et al. ......... | 433/218 |
| 5,118,296 A | 6/1992 | Eldred | |
| 5,151,044 A * | 9/1992 | Rotsaert ......................... | 433/229 |
| 5,162,130 A | 11/1992 | McLaughlin | |
| 5,342,201 A * | 8/1994 | Oden ............................. | 433/223 |
| 5,639,239 A * | 6/1997 | Earle ............................. | 433/218 |
| 6,254,385 B1 * | 7/2001 | Jung et al. ..................... | 433/26 |
| 6,371,762 B1 | 4/2002 | Foser | |
| 6,672,871 B2 * | 1/2004 | Hurson ......................... | 433/172 |
| 2004/0096805 A1 | 5/2004 | Saito et al. | |
| 2004/0158342 A1 | 8/2004 | Wolf et al. | |
| 2004/0161726 A1 | 8/2004 | Saito et al. | |
| 2005/0064369 A1 | 3/2005 | Zel et al. | |

FOREIGN PATENT DOCUMENTS

| | | |
|---|---|---|
| DE | 197 14 759 | 10/1998 |
| DE | 198-53-949 A1 | 5/2000 |
| DE | 199 44 130 | 4/2001 |
| DE | 101-45-104 A1 | 1/2003 |
| EP | 1 400 232 | 3/2004 |
| EP | 1454596 | 9/2004 |

OTHER PUBLICATIONS

Abstract of DE 19714759.

(Continued)

*Primary Examiner* — Ralph Lewis
(74) *Attorney, Agent, or Firm* — Fitzpatrick, Cella, Harper & Scinto

(57) ABSTRACT

A method of producing a dental prosthetic item 3, wherein the dental prosthetic item 3 is attached, via an interior surface 5, to another dental prosthetic item 2 by means of an adhesive 9, and for adhesive 9 there is provided a gap 8 disposed between an interior surface of the dental prosthetic item 3 and the other dental prosthetic item 2, wherein interior surface 5 of the dental prosthetic item is designed to make allowance for the visual properties of adhesive 9. Furthermore, a dental prosthetic item 3 is produced on the above lines and a blank 41 for the production of such a dental prosthetic item 3 and the other dental prosthetic item 2 is disclosed.

8 Claims, 3 Drawing Sheets

OTHER PUBLICATIONS

Abstract of DE 19944130.
English Abstract of EP 1454596.
Chinese Office Action dated Oct. 30, 2009 in Chinese Patent Application No. 200680016408.

"Panavia F 2.0: The Dual Cure Dental Adhesive System that's perfect for ANY procedure and ANY curing light!", Kuraray Dental, 2003.
"Panavia F 2.0: Kuraray", First Look, Reality Publishing, 2004.
"3M ESPE: RelyX Veneer Cement System", 3M, 2001.

* cited by examiner

METHOD OF PRODUCING A DENTAL PROSTHETIC ITEM, AND DENTAL PROSTHETIC ITEM THUS PRODUCED

TECHNICAL FIELD

The invention relates to a method of producing a dental prosthetic item, which prosthetic item is attached to another prosthetic item via an interior surface. The method involves, in particular, the production of a dental prosthetic item using a CAD/CAM program. The invention further relates to a dental prosthetic item thus produced.

DESCRIPTION OF THE RELATED ART

In classical dental technology, crowns and bridges are fabricated by producing a framework that is subsequently faced with a veneer. The veneer serves to produce a highly aesthetic result. The production of the framework can be effected via CAD/CAM procedures, but the veneer must be applied manually.

Furthermore, it is known to make crowns from homogeneous blanks by means of CAD/CAM procedures. A certain degree of aesthetic adaptation can be achieved by appropriate selection of the color of the blank, but an optimal aesthetic result cannot be attained. Although the coloration of a solid, ground crown is improved somewhat when use is made of blanks that have a color gradient, exact matching is again not possible.

Furthermore, it is known to automatically apply different materials having different visual characteristics to a framework in order to produce the desired aesthetic appearance and the shape predetermined by the CAD data set. To this end, EP 1,400,232 A1 discloses that a dental prosthetic item having an aesthetic natural appearance can be produced by superimposing a number of layers, of which the bottom layers are opaque and at least one of the bottom layers is iridescent, whilst the surface layers are predominantly transparent and iridescent.

The object to be achieved by the invention is to provide a dental prosthetic item involving denture parts produced by grinding which is aesthetically on a par with the classical layer-by-layer veneering technique that is the norm in dental technology.

SUMMARY AND OBJECTS OF THE INVENTION

In the inventive method of producing a dental prosthetic item that, for example, is to be attached to an other dental prosthetic item by means of an adhesive, a gap is provided between the interior surface of the first dental prosthetic item and the other dental prosthetic item, the interior surface of the prosthetic item being designed to make allowances for the visual characteristics of the adhesive.

By dividing a complete dental prosthetic item, such as a crown, into several parts with one of these parts being produced by the aforementioned procedure, the advantage gained is that the individual parts can be shaped in accordance with the respective requirements. High demands regarding strength and biocompatibility are placed on the core of a complete dental prosthetic item, whereas the visual, haptic, and abrasive characteristics are more important with respect to the visible parts of the dental prosthetic item.

By dividing the dental prosthetic item into a number of parts, it is further possible to produce a gap of varying width between the parts, so that when adhesively joining the parts together, said width will be matched to the layer of adhesive.

When producing a crown from a framework and an external part and subsequently joining these parts together with a dyed adhesive, color matching can be achieved if the external part is translucent like tooth enamel. The colored layer under the external part shines through and produces the desired color effect, which is similar to a natural tooth.

The thickness of the adhesive layer is set in such a way that the desired color intensity and/or coloration are attained, since these depend on the thickness of the adhesive layer. If a thick adhesive layer is used, the visual impression is usually darker than with a thinner layer of adhesive.

The thickness of the layer of adhesive along the interface between two parts can differ very widely. A natural tooth is usually darker in its lower region than in its upper region. The adhesive layer is therefore typically designed to be thicker in the lower region of a dental prosthetic item.

In accordance with a further development, the coloration and/or color intensity of the dyed adhesive layer can be influenced after joining the parts and establishing an adhesive bond.

This influence on coloration and/or color intensity is advantageously achieved by irradiating the adhesive layer with light, in particular with light of a wavelength outside the visible range. The color of the dental prosthetic item can thus be matched to the existing teeth.

An advantageous feature for positioning the individual parts relatively to each other and creating an adhesive layer with the desired color characteristics is to provide at least one of the parts with contact surfaces disposed on protrusions to form a spacer. These spacers should be placed in regions that are not visible or only slightly visible.

The spacer delimits the gap to a predetermined width. The adhesive layer is located within this gap.

For the purpose of positioning one part relatively to the other it is advantageous to provide mating surfaces that enable precise and unambiguous alignment of the parts.

Furthermore, it may be advantageous to allow a CAD program to automatically propose how to divide up the dental prosthetic item to be fabricated. Using CAD procedures for the fabrication of a dental prosthetic item, it is possible to let the software select the interface between the at least two parts of the dental prosthetic item, making allowances for both the minimum size and the profile of the mating contours and for the provision of an interstice between the parts, the width of which can be varied on the basis of aesthetic criteria. The two parts can be composed of the materials that are most suitable for the purpose.

Fabrication can be advantageously simplified by using a single block in which several types of material are combined, so that both of the necessary parts can be fabricated in a single milling operation without interim intervention.

The invention further relates to a dental prosthetic item for attachment to the stump of a tooth or to another dental prosthetic item, which first dental prosthetic item has a visible exterior surface and an interior surface suitable for attachment by means of an adhesive, said interior surface intended for the attachment of the dental prosthetic item being designed such that a gap is present for applying the adhesive between the internal surface of the dental prosthetic item and the stump of the tooth or the other dental prosthetic item. The internal surface of the dental prosthetic item is designed to make allowance for the visual characteristics of the adhesive.

Advantageously, the interior surface of the dental prosthetic item is shaped such that a gap width governed by a desired appearance is present between the interior surface of the dental prosthetic item and the stump of the tooth or the other dental prosthetic item. This makes it possible to manipulate the appearance even for given external dimensions.

It has proven to be particularly advantageous if the dental prosthetic item is translucent and the adhesive is visually perceptible through the dental prosthetic item. In this manner it is particularly easy to effect manipulation of the visual characteristics.

An advantageous development of the dental prosthetic item provides at least one spacer on the dental prosthetic item for alignment thereof relatively to the stump of a tooth or to said other dental prosthetic item. Thus the dental prosthetic item can be positioned particularly easily relatively to the other dental prosthetic item or to the stump of a tooth, and the desired layer thickness of adhesive can be adjusted particularly well.

Mating surfaces are advantageously provided on the dental prosthetic item, these serving to orient the dental prosthetic item relatively to the stump of a tooth or to the other dental prosthetic item and thereby enable precise and unambiguous alignment of the dental prosthetic items. This increases positioning accuracy even further.

A further object of the invention is a blank for the fabrication of a dental prosthetic item which consists of a number of parts and is to be carved from the blank by a material-removal machining technique. The blank consists of a first portion of a first material for the other dental prosthetic item and of a second portion of a second material for the dental prosthetic item. This enables simultaneous sequential fabrication of both dental prosthetic items in a single pass in the same machining equipment.

Advantageously, the material used for the other dental prosthetic item is $Al_2O_3$ or ZrO, and the material used for the dental prosthetic item comprises feldspar ceramics. Both materials are particularly suitable for the respective applications.

In a particularly advantageous embodiment, the part of the blank used for the fabrication of the dental prosthetic item exhibits regions of different coloration. Therefore it is possible to reduce the thickness of the layer of adhesive necessary for the production of an aesthetic surface.

BRIEF DESCRIPTION OF THE DRAWINGS

Exemplary embodiments of the invention are illustrated in the drawings, in which.

DETAILED DESCRIPTION OF EXEMPLARY EMBODIMENTS OF THE INVENTION

Figure 1:
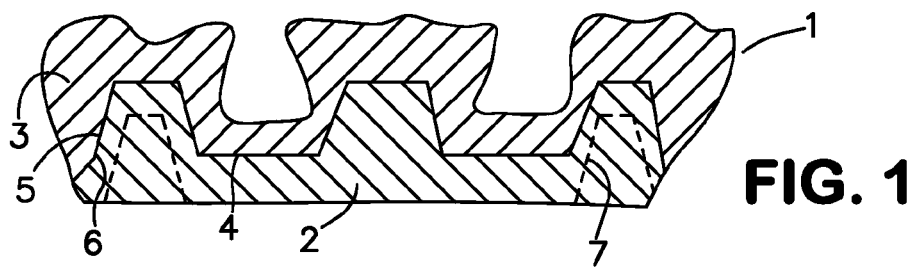
FIG. 1 shows a dental prosthetic item comprising a bridge and a veneer.

FIG. 1 shows a complete dental prosthetic item 1 as is to be fabricated, depicted in the form of a bridge, which is composed of a further dental prosthetic item in the form of a framework 2 and a dental prosthetic item of the invention in the form of a veneer 3. Between veneer 3 and framework 2 there is an interface 4 formed by the interior surface 5 of veneer 3 on one side and by the exterior surface 6 of frame 2 on the other. The profile of interface 4 is preferably specified automatically by a CAD program making allowances for the necessary design parameters.

Veneer 3 is fabricated from a translucent material which allows the layers beneath veneer 3 to shine through.

Framework 2 can itself exhibit an interior surface 7 for attachment to an abutment (not shown) or a tooth residue (not shown).

Figure 2:
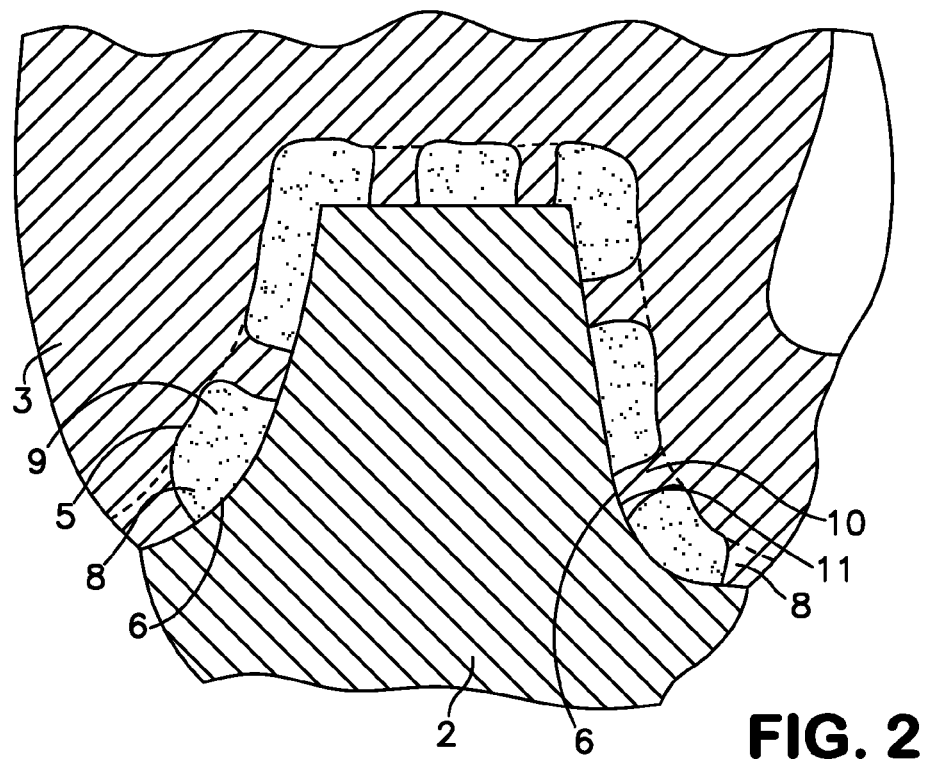
FIG. 2 shows a detail of FIG. 1 in the region of an internal interface.

FIG. 2 shows the profile of the interface in detail and illustrates the provision of a gap 8 between the interior surface 5 of veneer 3 and the exterior surface 6 of framework 2, said gap being filled with an adhesive 9.

In order to achieve a defined layer thickness of the adhesive layer, a protrusion 10 is located in gap 8, which protrusion bears against said exterior surface 6 by means of a contact surface 11.

Adhesive 9 is dyed and exhibits a color intensity and/or a coloration that depend on the thickness of the adhesive layer. If the layer thickness is increased, the color intensity increases and the adhesive layer appears darker. With a decreasing layer thickness, the color intensity decreases and the adhesive layer appears brighter.

Of course, adhesive 9 can be available in different basic colors and be selected in an appropriate way in order to obtain the desired color effects after having been introduced into the gap. The colors in the adhesive 9 shine through the translucent veneer 3.

Figure 3:
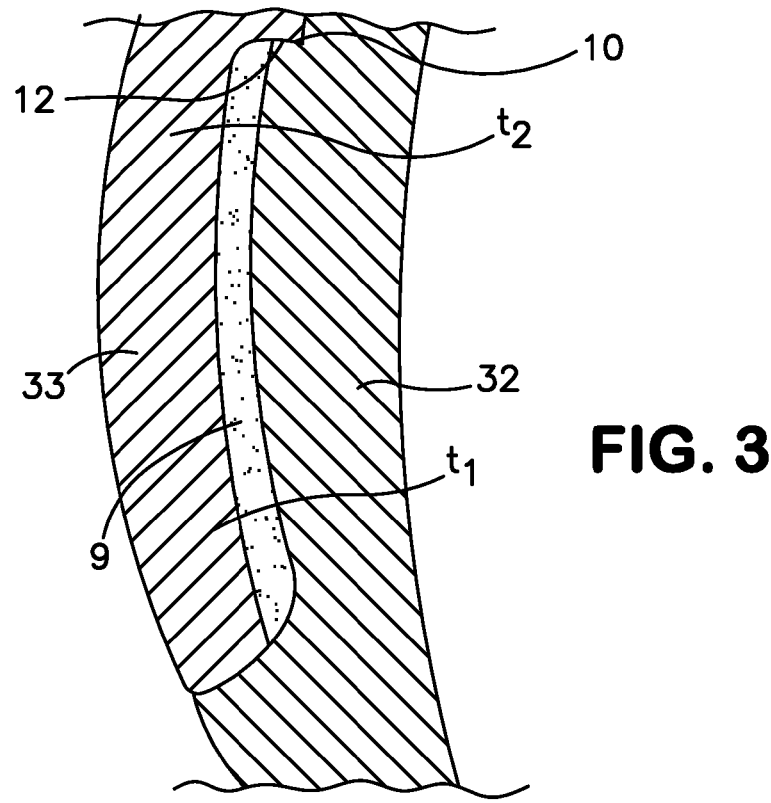
FIG. 3 shows another dental prosthetic item.

FIG. 3 shows a tooth restoration, in which an exterior part 33 is attached to an interior part 32. This is achieved by filling a gap 8 with an adhesive layer 9, whose width $t_1$ in a lower region is greater than its width $t_2$ in an upper region.

The exterior part is positioned relatively to the interior part at the predefined distance therefrom by means of a spacer element 10 on the exterior part 33, which engages an appropriate recess 12 on the interior part 32.

Figure 4:
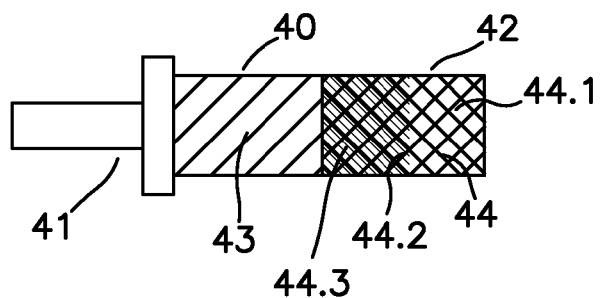
FIG. 4 shows a blank with various material characteristics for the fabrication of parts of a dental prosthetic item.

FIG. 4 depicts a blank for the fabrication of a dental prosthetic item consisting of several parts, the blank 40 itself comprising a handle 41 and a corpus 42.

Corpus 42 has two subregions 43, 44 exhibiting different material compositions. The differences in material composition may reside both in their visual characteristics, for example color or translucence, and in their mechanical properties, so that one component of a split dental prosthetic item can be made from one material and another component from the other material of subregion 44 at only one chuck setting and without having to change the tool.

The portion 44 intended for the fabrication of said second component 3 features differently colored regions 44.1-44.3.

In principle, the advantage produced by the invention can also be achieved when applying an undivided dental prosthetic item, for example a veneer, to a restored tooth, by using a color matched adhesive layer. The dental prosthetic item can also be provided, at the interface, with a gap, into which spacers project. The width of the gap and thus of the adhesive layer can be adapted by the design software according to the desired color profile, so that when the dental prosthetic item is mounted, the first step comprises applying an adequate quantity of adhesive. When the dental prosthetic item is pressed onto the stump of a tooth, the surplus adhesive will be squeezed out through the interstice and can be removed. When pressing, care must be taken to ensure that the required stop position is actually reached, so that the predetermined thickness of the adhesive layer is attained and not exceeded.

The adhesive can theoretically be organic or inorganic. In the case of an inorganic adhesive, the material used can be dyed solder glass, for example.

Figure 5A:
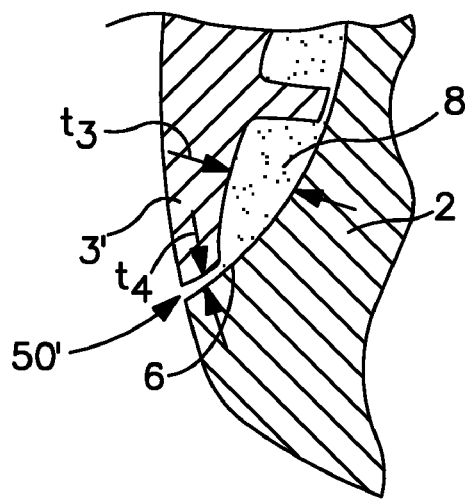
FIGS. 5A to 5C show sections of the dental prosthetic item of FIG. 1, each with a different design of the marginal region.
Figure 5B:
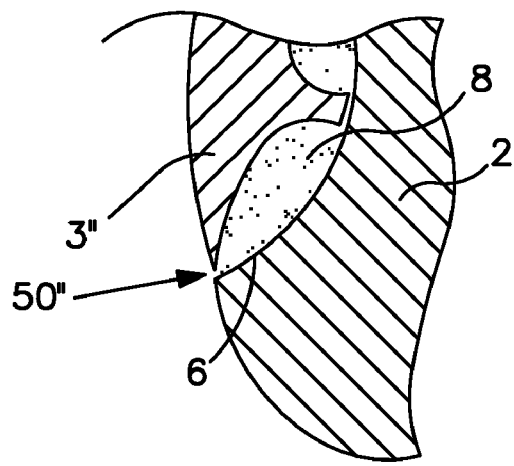
Figure 5C:
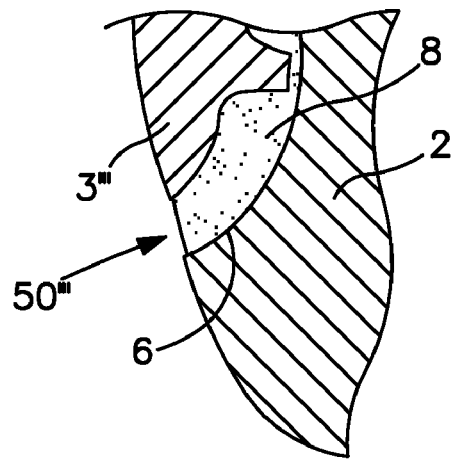

FIGS. 5A to 5C show different options for the design of the transition region 50', 50", 50''' between veneer 3', 3", 3''' and framework 2. Such a transition region 50', 50", 50''' must fulfill several requirements. First of all it must be smooth, so that there is no risk of injury, or so that no moisture and/or harmful microorganisms can settle therein. Secondly, if it is in the anterior teeth region, it must be as invisible as possible in order not to disturb the overall aesthetic appearance. This primarily requires that adhesive layer 9 shines through uniformly, which in turn depends on the thickness of veneer 3', 3", 3''' and also on the thickness of the adhesive layer in the marginal region. Furthermore, the entire dental prosthetic item must also be able to withstand all stresses in the transition region 50', 50", 50'''.

To achieve this, it is now possible to form the transition region 50' as a truncated conical transition region 50', as shown in FIG. 5A.

The truncated conical transition region 50' is filled with a thin adhesive layer right up to the exterior visible edge of veneer 3'. The layer thickness $t_4$, usually between 1 and 10 μm, is approximately one order of magnitude smaller than the average layer thickness of the adhesive layer $t_3$ in the rest of the region between the interior surface of veneer 3' and the exterior surface of the framework. Due to its minimal thickness $t_4$, the adhesive layer 9 is only very faintly perceptible from the outside, whereby very good visual characteristics are achieved. Furthermore, it is possible with this type of transition to keep layer thickness $t_3$ of adhesive layer 9 relatively constant right down to the region of the transition region 50', which makes for a homogeneous color profile. The fact that the adhesive layer extends as far as the exterior of veneer 3' means that veneer 3' is additionally sealed. Thus very good hygienic characteristics are attained.

The advantage of a transition region 50" providing a thin boundary wall of veneer 3", as shown in FIG. 5B, is that while maintaining good visual characteristics, high sealing efficiency is also achieved.

Alternatively, the transition region 50''' can be in the form shown in FIG. 5C. This provides constant thickness of adhesive 9 up to the marginal region. The advantage of this transition region 50''' is that it is very smooth, on the one hand, and very dense on the other hand.

The invention claimed is:

1. A method of manipulating a dental prosthetic item, comprising the steps of:
    providing a translucent dental prosthetic item, the dental prosthetic item including an interior surface;
    attaching the dental prosthetic item, via the interior surface, to a stump of a tooth or another dental prosthetic item using a layer of an adhesive in a gap between the interior surface of the dental prosthetic item and the stump or other dental prosthetic item, the interior surface of the dental prosthetic item being shaped such that a width of the gap at a transition region between the dental prosthetic item and the stump or another dental prosthetic item is less than an average width of the gap across a remaining region of the gap;
    establishing an adhesive bond between the dental prosthetic item and the stump or other dental prosthetic item, using the adhesive, whereby the width of the layer of the adhesive in the gap at the transition region is less than an average width of the layer of the adhesive in the gap across the remaining region of the gap; and
    after establishing the adhesive bond, treating the adhesive to change at least one of coloration and color intensity of the adhesive and change visual characteristics of the attached dental prosthetic item.

2. The method as defined in claim 1, wherein treating the adhesive after establishing the adhesive bond includes irradiating the adhesive with light to influence the coloration and/or color intensity of the adhesive.

3. The method as defined in claim 2, wherein the light has a wavelength outside the visible range.

4. The method as defined in claim 1, wherein a thickness of the layer of adhesive exhibits local difference.

5. The method as defined in claim 1, wherein the dental prosthetic item is oriented toward the other dental prosthetic item by means of at least one spacer, wherein the spacer is part of the interior surface of the dental prosthetic item and wherein the spacer is disposed in non-visible regions.

6. The method as defined in claim 1, wherein mating surfaces are provided on the dental prosthetic item for the purpose of orienting the dental prosthetic item relative to the stump or other dental prosthetic item to make exact and unambiguous alignment of the dental prosthetic item possible.

7. The method as defined in claim 1, further comprising determining at least a first width and a second width of the layer of the adhesive, the first width being different from the second width.

8. The method as defined in claim 7, wherein the first and second widths are determined, at least in part, based on desired visual properties of the dental prosthetic item and visual properties of the adhesive.

\* \* \* \* \*